(12) United States Patent
Oosawa

(10) Patent No.: US 12,249,113 B2
(45) Date of Patent: Mar. 11, 2025

(54) IMAGE PROCESSING DEVICE, IMAGE PROCESSING METHOD, AND IMAGE PROCESSING PROGRAM

(71) Applicant: FUJIFILM Corporation, Tokyo (JP)

(72) Inventor: Akira Oosawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 414 days.

(21) Appl. No.: 17/709,405

(22) Filed: Mar. 30, 2022

(65) Prior Publication Data
US 2022/0222917 A1 Jul. 14, 2022

Related U.S. Application Data

(63) Continuation of application No. PCT/JP2020/033315, filed on Sep. 2, 2020.

(30) Foreign Application Priority Data

Oct. 7, 2019 (JP) .................. 2019-184534

(51) Int. Cl.
*G06V 10/75* (2022.01)
*G06T 7/00* (2017.01)
*G06V 10/82* (2022.01)

(52) U.S. Cl.
CPC .......... *G06V 10/751* (2022.01); *G06T 7/0016* (2013.01); *G06V 10/82* (2022.01);
(Continued)

(58) Field of Classification Search
CPC .... G06V 10/751; G06V 10/82; G06T 7/0016; G06T 2207/10072; G06T 2207/30061
See application file for complete search history.

(56) References Cited

U.S. PATENT DOCUMENTS

2011/0190633 A1 8/2011 Kawagishi et al.
2017/0090739 A1* 3/2017 Kozuka ............... G16H 30/20
(Continued)

FOREIGN PATENT DOCUMENTS

JP  2004046594  2/2004
JP  3577680  10/2004
(Continued)

OTHER PUBLICATIONS

Joseph Jacob et al., "Evaluation of computer-based computer tomography stratification against outcome models in connective tissue disease-related interstitial lung disease: a patient outcome study," BMC Medicine (2016), vol. 14, Nov. 2016, pp. 1-13.
(Continued)

*Primary Examiner* — John J Lee
(74) *Attorney, Agent, or Firm* — JCIPRNET

(57) ABSTRACT

An image processing device, an image processing method, and an image processing program make it possible to accurately recognize property changes between medical images having different imaging times. A property classification unit classifies each pixel included in a target region of each of a first medical image and a second medical image of which an imaging time is later than an imaging time of the first medical image for the same subject into any one of a plurality of types of properties. A quantitative value derivation unit specifies property pairs each representing a property change between corresponding pixels in at least partial regions within the target regions, and derives a quantitative value in the at least partial regions for each of the property pairs.

14 Claims, 12 Drawing Sheets

(52) U.S. Cl.
CPC .............. *G06T 2207/10072* (2013.01); *G06T 2207/30061* (2013.01)

(56) References Cited

U.S. PATENT DOCUMENTS

| | | | |
|---|---|---|---|
| 2018/0289336 A1* | 10/2018 | Osawa | G06T 7/0012 |
| 2019/0086741 A1* | 3/2019 | Milton | G02F 1/134309 |
| 2020/0237452 A1* | 7/2020 | Wolf | G06F 3/048 |

FOREIGN PATENT DOCUMENTS

| | | |
|---|---|---|
| JP | 5661453 | 1/2015 |
| JP | 2015167629 | 9/2015 |
| JP | 2017068837 | 4/2017 |
| JP | 2018175227 | 11/2018 |

OTHER PUBLICATIONS

Wasawa Tae, "Quantitative evaluation of CT images of interstitial pneumonia by computer" with English abstract, Journal of Japanese Association of Tomography, vol. 41, Aug. 2014, pp. 1-11.
"International Search Report (Form PCT/ISA/210) of PCT/JP2020/033315," mailed on Nov. 10, 2020, with English translation thereof, pp. 1-5.
"Written Opinion of the International Searching Authority (Form PCT/ISA/237)" of PCT/JP2020/033315, mailed on Nov. 10, 2020, with English translation thereof, pp. 1-6.

* cited by examiner

FIG. 5

| PROPERTY TYPE | EVALUATION VALUE |
|---|---|
| CYST | 2.9 |
| GROUND GLASS OPACITY | 7.6 |
| RETICULAR OPACITY | 8.5 (MAXIMUM) |
| BRONCHIECTASIS | 3.2 |
| . . . | . . . |
| . . . | . . . |
| NORMAL LUNG | -7.1 |
| LOW DENSITY | -12.3 |

FIG.7

| G1\G2 | NORMAL OPACITY | GROUND GLASS OPACITY | RETICULAR OPACITY | CONSOLIDATION | HONEYCOMB LUNG | HYPERLUCENT LUNG | NODULAR OPACITY | OTHER | BRONCHUS | BLOOD VESSEL | TOTAL |
|---|---|---|---|---|---|---|---|---|---|---|---|
| NORMAL OPACITY | 25% | 10% | 0 | 0 | 0 | 5% | 0 | 0 | 5% | 0 | 45% |
| GROUND GLASS OPACITY | 0 | 5% | 10% | 0 | 0 | 0 | 0 | 0 | 0 | 0 | 15% |
| RETICULAR OPACITY | 0 | 0 | 10% | 0 | 5% | 0 | 0 | 0 | 0 | 0 | 15% |
| CONSOLIDATION | 0 | 0 | 0 | 5% | 0 | 0 | 0 | 0 | 0 | 0 | 5% |
| HONEYCOMB LUNG | 0 | 0 | 0 | 0 | 3% | 0 | 0 | 0 | 0 | 0 | 3% |
| HYPERLUCENT LUNG | 0 | 0 | 0 | 0 | 0 | 0 | 0 | 0 | 0 | 0 | 0% |
| NODULAR OPACITY | 0 | 0 | 0 | 0 | 0 | 0 | 2% | 0 | 0 | 0 | 2% |
| OTHER | 0 | 0 | 0 | 0 | 0 | 0 | 0 | 5% | 0 | 0 | 5% |
| BRONCHUS | 0 | 0 | 0 | 0 | 0 | 0 | 0 | 0 | 5% | 0 | 5% |
| BLOOD VESSEL | 0 | 0 | 0 | 0 | 0 | 0 | 0 | 0 | 0 | 5% | 5% |
| TOTAL | 25% | 15% | 20% | 5% | 8% | 5% | 2% | 5% | 10% | 5% | 100% |

FIG. 8

| G1\G2 | NORMAL OPACITY | GROUND GLASS OPACITY | RETICULAR OPACITY | CONSOLIDATION | HONEYCOMB LUNG | HYPERLUCENT LUNG | NODULAR OPACITY | OTHER | BRONCHUS | BLOOD VESSEL | TOTAL |
|---|---|---|---|---|---|---|---|---|---|---|---|
| NORMAL OPACITY | 25% | 10% | 0 | 0 | 0 | 5% | 0 | 0 | 5% | 0 | 45% |
| GROUND GLASS OPACITY | 0 | 5% | 10% | 0 | 0 | 0 | 0 | 0 | 0 | 0 | 15% |
| RETICULAR OPACITY | 0 | 0 | 10% | 0 | 5% | 0 | 0 | 0 | 0 | 0 | 15% |
| CONSOLIDATION | 0 | 0 | 0 | 5% | 0 | 0 | 0 | 0 | 0 | 0 | 5% |
| HONEYCOMB LUNG | 0 | 0 | 0 | 0 | 3% | 0 | 0 | 0 | 0 | 0 | 3% |
| HYPERLUCENT LUNG | 0 | 0 | 0 | 0 | 0 | 0 | 0 | 0 | 0 | 0 | 0% |
| NODULAR OPACITY | 0 | 0 | 0 | 0 | 0 | 0 | 2% | 0 | 0 | 0 | 2% |
| OTHER | 0 | 0 | 0 | 0 | 0 | 0 | 0 | 5% | 0 | 0 | 5% |
| BRONCHUS | 0 | 0 | 0 | 0 | 0 | 0 | 0 | 0 | 5% | 0 | 5% |
| BLOOD VESSEL | 0 | 0 | 0 | 0 | 0 | 0 | 0 | 0 | 0 | 5% | 5% |
| TOTAL | 25% | 15% | 20% | 5% | 8% | 5% | 2% | 5% | 10% | 5% | 100% |

FIG. 10

| G1\G2 | NORMAL OPACITY | GROUND GLASS OPACITY | RETICULAR OPACITY | CONSOLIDATION | HONEYCOMB LUNG | HYPERLUCENT LUNG | NODULAR OPACITY | OTHER | BRONCHUS | BLOOD VESSEL | TOTAL |
|---|---|---|---|---|---|---|---|---|---|---|---|
| NORMAL OPACITY | 25% | 10% | 0 | 0 | 0 | 5% | 0 | 0 | 5% | 0 | 45% |
| GROUND GLASS OPACITY | 0 | 5% | 10% | 0 | 0 | 0 | 0 | 0 | 0 | 0 | 15% |
| RETICULAR OPACITY | 0 | 0 | 10% | 0 | 5% | 0 | 0 | 0 | 0 | 0 | 15% |
| CONSOLIDATION | 0 | 0 | 0 | 5% | 0 | 0 | 0 | 0 | 0 | 0 | 5% |
| HONEYCOMB LUNG | 0 | 0 | 0 | 0 | 3% | 0 | 0 | 0 | 0 | 0 | 3% |
| HYPERLUCENT LUNG | 0 | 0 | 0 | 0 | 0 | 0 | 0 | 0 | 0 | 0 | 0% |
| NODULAR OPACITY | 0 | 0 | 0 | 0 | 0 | 0 | 2% | 0 | 0 | 0 | 2% |
| OTHER | 0 | 0 | 0 | 0 | 0 | 0 | 0 | 5% | 0 | 0 | 5% |
| BRONCHUS | 0 | 0 | 0 | 0 | 0 | 0 | 0 | 0 | 5% | 0 | 5% |
| BLOOD VESSEL | 0 | 0 | 0 | 0 | 0 | 0 | 0 | 0 | 0 | 5% | 5% |
| TOTAL | 25% | 15% | 20% | 5% | 8% | 5% | 2% | 5% | 10% | 5% | 100% |

- 1  NORMAL OPACITY ⇒ NORMAL OPACITY ; 25%
- 2  NORMAL OPACITY ⇒ GROUND GLASS OPACITY ; 10%
- 2  GROUND GLASS OPACITY ⇒ RETICULAR OPACITY ; 10%
- 2  RETICULAR OPACITY ⇒ RETICULAR OPACITY ; 10%
- 5  NORMAL OPACITY ⇒ HYPERLUCENT LUNG ; 5%
- 5  NORMAL OPACITY ⇒ BRONCHUS ; 5%
- 5  RETICULAR OPACITY ⇒ HONEYCOMB LUNG ; 5%

~58

IMAGE PROCESSING DEVICE, IMAGE PROCESSING METHOD, AND IMAGE PROCESSING PROGRAM

CROSS-REFERENCE TO RELATED APPLICATIONS

This application is a Continuation of PCT International Application No. PCT/JP2020/033315 filed on Sep. 2, 2020, which claims priority under 35 U.S.C § 119(a) to Japanese Patent Application No. 2019-184534 filed on Oct. 7, 2019. Each of the above application(s) is hereby expressly incorporated by reference, in its entirety, into the present application.

BACKGROUND OF THE INVENTION

1. Field of the Invention

The present disclosure relates to an image processing device, an image processing method, and a non-transitory computer recording medium storing an image processing program.

2. Description of the Related Art

In recent years, with the progress of medical devices, such as a computed tomography (CT) device and a magnetic resonance imaging (MRI) device, high-resolution three-dimensional images with higher quality have been used for image diagnosis.

Meanwhile, interstitial pneumonia is known as a lung disease. In addition, there has been proposed a method of analyzing a CT image of a patient with interstitial pneumonia to classify lesions, such as honeycomb lung, reticular opacity, and cyst, and tissues, such as normal lungs, blood vessels, and bronchi, which are included in a lung field region of the CT image, as properties and to quantify the properties (see Evaluation of computer-based computer tomography stratification against outcome models in connective tissue disease-related interstitial lung disease: a patient outcome study, Joseph Jacob et al., BMC Medicine (2016) 14:190, DOI 10.1186/s12916-016-0739-7 and Quantitative evaluation of CT images of interstitial pneumonia by computer, Iwasawa Tae, Journal of Japanese Association of Tomography Vol. 41, No. 2, August 2014). In this manner, the CT image is analyzed, and the properties are classified, and the volume, area, number of pixels, and the like of the property are quantified, so that the degree of lung disease can be easily determined. In addition, for each property that is classified and quantified in this manner, different colors are assigned and displayed, so that it is possible to easily diagnose how much a region with a specific property is included in the image.

There has also been proposed a method of classifying each pixel of a medical image into a class for each of a plurality of properties using a discriminative model that is constructed by a deep learning method or the like. With such a discriminative model used, it is possible to classify a target pixel of an input medical image into any one of a plurality of types of properties.

Meanwhile, in order to diagnose the recovery or progression of the disease, there is a case in which comparative observation over time is performed using past medical images of the same patient. Upon such comparative observation over time, various methods have been proposed to make it easier to visually recognize changes over time. For example, JP2015-167629A has proposed a method of acquiring a plurality of images having different imaging dates, setting a reference point at a part of interest of each image, acquiring a measured value of a measurement item of the part of interest in any direction centered on the reference point, calculating an amount of time-series change of the measured value, and generating and displaying an annotation and a graph representing the amount of change during observation over time. Further, JP3577680B has proposed a method of obtaining a difference image between radiographic images of a chest having different imaging times, labeling a portion corresponding to a time-varying portion in the difference image, and expressing a time-varying region having a predetermined size or larger with a fill pattern or the like, thereby displaying the time-varying portion with an increased emphasis degree. Further, JP5661453B has proposed a method of displaying a motion picture after performing registration between corresponding parts in CT images having different imaging times.

SUMMARY OF THE INVENTION

However, in the methods described in JP2015-167629A, JP3577680B, and JP5661453B, only the difference between the images is emphasized and displayed. For this reason, in a case in which properties to be classified are a plurality of types as in the above-mentioned interstitial pneumonia, it is not possible to accurately grasp which property the past property has changed to.

The present disclosure has been made in view of the above circumstances, and an object thereof is to make it possible to accurately recognize property changes between medical images having different imaging times.

There is provided an image processing device according to the present disclosure comprising: a property classification unit that classifies each pixel included in a target region of each of a first medical image and a second medical image of which an imaging time is later than an imaging time of the first medical image for the same subject into any one of a plurality of types of properties; and a quantitative value derivation unit that specifies property pairs each representing a property change between corresponding pixels in at least partial regions within the target regions, and derives a quantitative value in the at least partial regions for each of the property pairs.

The "property pair representing a property change between corresponding pixels" means a combination of the property for the first medical image and the property for the second medical image that are derived in the target regions included in the first medical image and the second medical image. For example, in a case in which a certain pixel in the first medical image is a property A and a pixel in the second medical image corresponding to the pixel is a property B, the property of the pixel is changed from the property A to the property B, so that the property pair is (A, B). In addition, the "property pair representing a property change between corresponding pixels" includes a combination of the properties in which there is no change in the property.

In the image processing device according to the present disclosure, the quantitative value derivation unit may derive a ratio in the at least partial regions for each of the property pairs as the quantitative value.

In addition, the image processing device according to the present disclosure may further comprise a registration unit that performs registration of the target regions between the first medical image and the second medical image.

Further, in the image processing device according to the present disclosure, the quantitative value derivation unit may derive an amount of change per unit time in an amount of the property pair between the corresponding pixels in the at least partial regions as the quantitative value.

As the "amount of the property pair", for example, the volume, area, and number of pixels of the property pair, and the ratio of the property pair to the target regions may be used.

Further, in the image processing device according to the present disclosure, the quantitative value derivation unit may divide the target region into a plurality of small regions and derive the quantitative value for each of the small regions.

In addition, the image processing device according to the present disclosure may further comprise a display control unit that displays the quantitative value for each of the property pairs on a display unit.

Further, in the image processing device according to the present disclosure, the display control unit may display the quantitative value such that a property pair in which a symptom is worsened, a property pair in which the symptom is improved, and a property pair in which there is no change in the symptom, out of the property pairs, can be identified.

Alternatively, in the image processing device according to the present disclosure, the display control unit may display the quantitative value for each of the property pairs in descending order of the quantitative values.

Alternatively, in the image processing device according to the present disclosure, the display control unit may superimpose and display information representing the quantitative value for at least a part of the property pairs, on the target region of the first medical image or the second medical image.

Further, in the image processing device according to the present disclosure, the property classification unit may have a discriminative model in which machine learning has been performed so as to classify the plurality of types of properties, and may classify each pixel included in the target region into any one of the plurality of types of properties via the discriminative model.

Further, in the image processing device according to the present disclosure, the target region may be a lung field region.

There is provided an image processing method according to the present disclosure comprising: classifying each pixel included in a target region of each of a first medical image and a second medical image of which an imaging time is later than an imaging time of the first medical image for the same subject into any one of a plurality of types of properties; and specifying property pairs each representing a property change between corresponding pixels in at least partial regions within the target regions, and deriving a quantitative value in the at least partial regions for each of the property pairs.

A non-transitory computer recording medium storing a program causing a computer to execute the image processing method according to the present disclosure may also be provided.

There is provided another image processing device according to the present disclosure comprising: a memory that stores a command to be executed by a computer; and a processor configured to execute the stored command, in which the processor executes classifying each pixel included in a target region of each of a first medical image and a second medical image of which an imaging time is later than an imaging time of the first medical image for the same subject into any one of a plurality of types of properties; and specifying property pairs each representing a property change between corresponding pixels in at least partial regions within the target regions, and deriving a quantitative value in the at least partial regions for each of the property pairs.

According to the present disclosure, it is possible to accurately recognize property changes between medical images having different imaging times.

BRIEF DESCRIPTION OF THE DRAWINGS

FIG. 5 is a view showing evaluation values corresponding to property types for a certain pixel.

FIG. 7 is a view showing a derivation result of the quantitative value.

FIG. 8 is a view showing a display screen of the quantitative value for each of property pairs.

FIG. 10 is a view showing a display screen of a list in which colors corresponding to the magnitude of the quantitative values are assigned, for each field of the property pairs.

DESCRIPTION OF THE PREFERRED EMBODIMENTS

Figure 1:
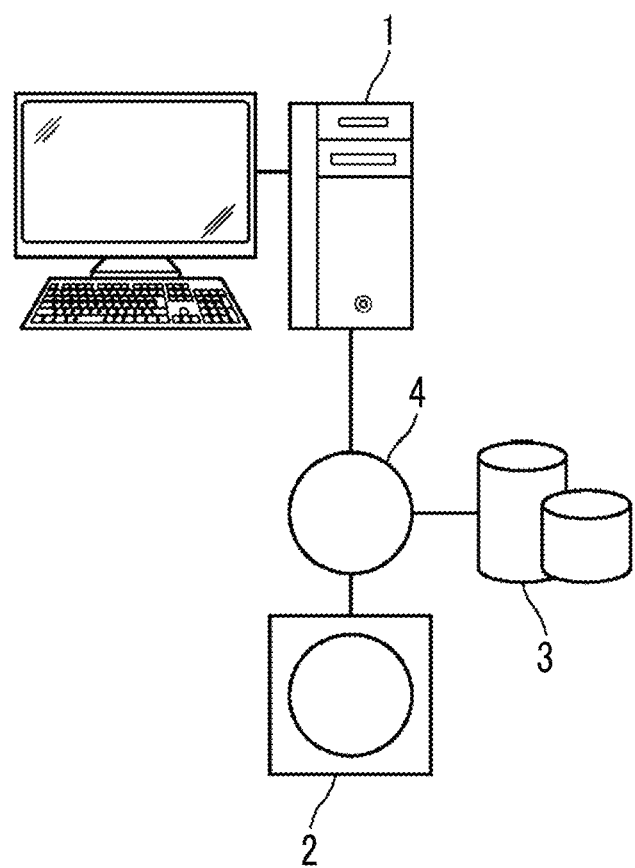
FIG. 1 is a hardware configuration view showing an outline of a diagnostic support system to which an image processing device according to an embodiment of the present disclosure is applied.

Hereinafter, an embodiment of the present disclosure will be described with reference to the drawings. FIG. 1 is a hardware configuration view showing an outline of a diagnostic support system to which an image processing device according to the embodiment of the present disclosure is applied. As shown in FIG. 1, in the diagnostic support system, an image processing device 1, a three-dimensional image capturing device 2, and an image storage server 3 according to the present embodiment are connected to communicate with each other through a network 4.

The three-dimensional image capturing device 2 is a device that generates a three-dimensional image showing a part, which is a part to be diagnosed of a subject, by imaging the part. Specifically, the three-dimensional image capturing device 2 is a CT device, an MM device, a positron emission tomography (PET) device, or the like. The three-dimensional image consisting of a plurality of slice images, which is generated by the three-dimensional image capturing device 2, is transmitted to the image storage server 3 and is stored thereon. In the present embodiment, the diagnostic target part of the patient who is a subject is the lungs, and the three-dimensional image capturing device 2 is a CT device and generates a CT image of the chest including the lungs of the subject as a three-dimensional image.

The image storage server 3 is a computer that stores and manages various kinds of data, and comprises a large-capacity external storage device and software for database management. The image storage server 3 communicates with other devices through the wired or wireless network 4 to transmit and receive image data or the like. Specifically, the image storage server 3 acquires various kinds of data including the image data of a medical image generated by the three-dimensional image capturing device 2 through the network, and stores the various kinds of data on a recording medium, such as a large-capacity external storage device, and manages the various kinds of data. The storage format of the image data and the communication between devices through the network 4 are based on a protocol, such as digital imaging and communications in medicine (DICOM). In the present embodiment, the image storage server 3 stores and manages a plurality of medical images having different imaging dates for the same patient.

The image processing device 1 of the present embodiment is realized by installing an image processing program of the present embodiment on one computer. The computer may be a workstation or a personal computer that is directly operated by a doctor who performs a diagnosis, or may be a server computer connected to the workstation or to the personal computer through a network. The image processing program is stored in a storage device of a server computer connected to the network or in a network storage so as to be accessible from the outside, and is downloaded and installed on a computer that the doctor uses in response to a request. Alternatively, the image processing program is distributed by being recorded on a recording medium, such as a digital versatile disc (DVD) or a compact disc read only memory (CD-ROM), and is installed onto the computer from the recording medium.

Figure 2:
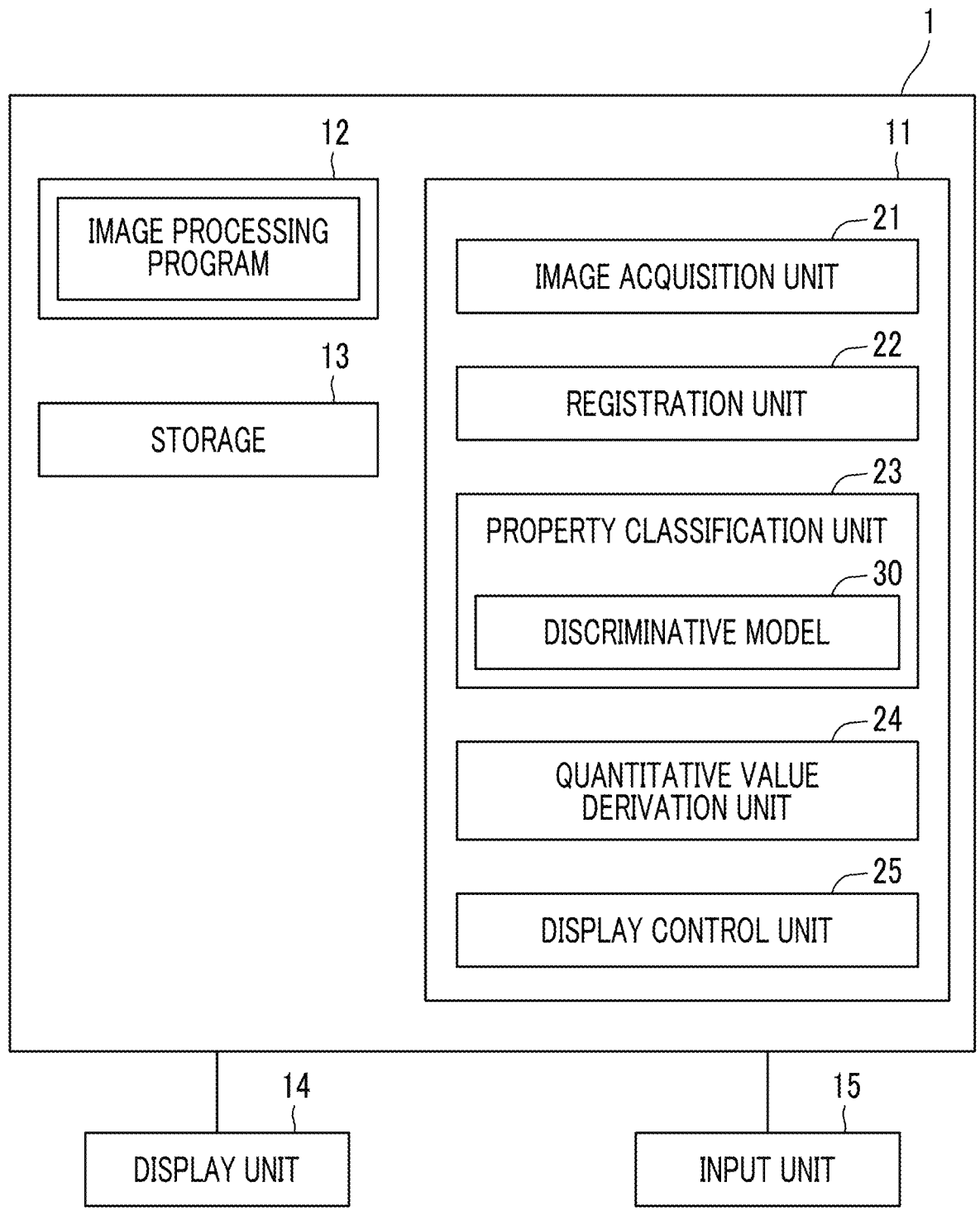
FIG. 2 is a schematic block diagram showing a configuration of the image processing device according to the present embodiment.

FIG. 2 is a diagram showing a schematic configuration of the image processing device that is realized by installing the image processing program on a computer. As shown in FIG. 2, the image processing device 1 comprises a central processing unit (CPU) 11, a memory 12, and a storage 13, as a configuration of a standard workstation. Further, a display unit 14, such as a liquid crystal display, and an input unit 15, such as a keyboard and a mouse, are connected to the image processing device 1.

The storage 13 includes a hard disk drive or the like, and stores the plurality of medical images of the same subject that are used to perform observation over time, which are acquired from the image storage server 3 through the network 4, and various information including information required for processing.

Further, the image processing program read out from the storage 13 by the CPU or the like is temporarily stored in the memory 12. The image processing program defines, as processing to be executed by the CPU 11, image acquisition processing of acquiring a first medical image G1 and a second medical image G2 of which an imaging time is later than an imaging time of the first medical image G1 for the same subject, registration processing of performing registration of target regions between the first medical image G1 and the second medical image G2, property classification processing of classifying each pixel included in the target region of each of the first medical image G1 and the second medical image G2 into any one of a plurality of types of properties, quantitative value derivation processing of specifying property pairs each representing a property change between corresponding pixels in at least partial regions within the target regions and deriving a quantitative value in the at least partial regions for each of the property pairs, and display control processing of displaying the quantitative value for each of the property pairs on a display unit 14.

Then, the CPU 11 executes the processing in accordance with the image processing program, so that the computer functions as an image acquisition unit 21, a registration unit 22, a property classification unit 23, a quantitative value derivation unit 24, and a display control unit 25.

The image acquisition unit 21 acquires the first medical image G1 and the second medical image G2 from the image storage server 3 through an interface (not shown) connected to the network. In the present embodiment, it is assumed that the first medical image G1 and the second medical image G2 are CT images including the lung field for the same subject. The acquired first and second medical images G1 and G2 are stored in the storage 13. In the present embodiment, it is assumed that the target region is a lung field region.

Here, in the first medical image G1 and the second medical image G2, there are differences in size and position of the target region between the images because of changes in the breathing and posture of the patient, which is the subject, and changes in the imaging field of view (FOV). Therefore, the registration unit 22 performs registration of the target regions of the first medical image G1 and the second medical image G2, that is, the lung field regions. Specifically, first, the imaging fields of view of the first medical image G1 and the second medical image G2 are matched with each other, and then the pixel densities are matched with each other. Then, the shift direction and shift amount of the corresponding pixel position are derived between the first medical image G1 and the second medical image G2. Then, registration between the lung field regions of the first and second medical images G1 and G2 is performed by non-linearly converting at least one of the lung field region of the first medical image G1 or the lung field region of the second medical image G2 based on the derived shift direction and shift amount. As the registration method, any method such as template matching, warping, rigid body registration, or non-rigid body registration can be used.

Figure 3:
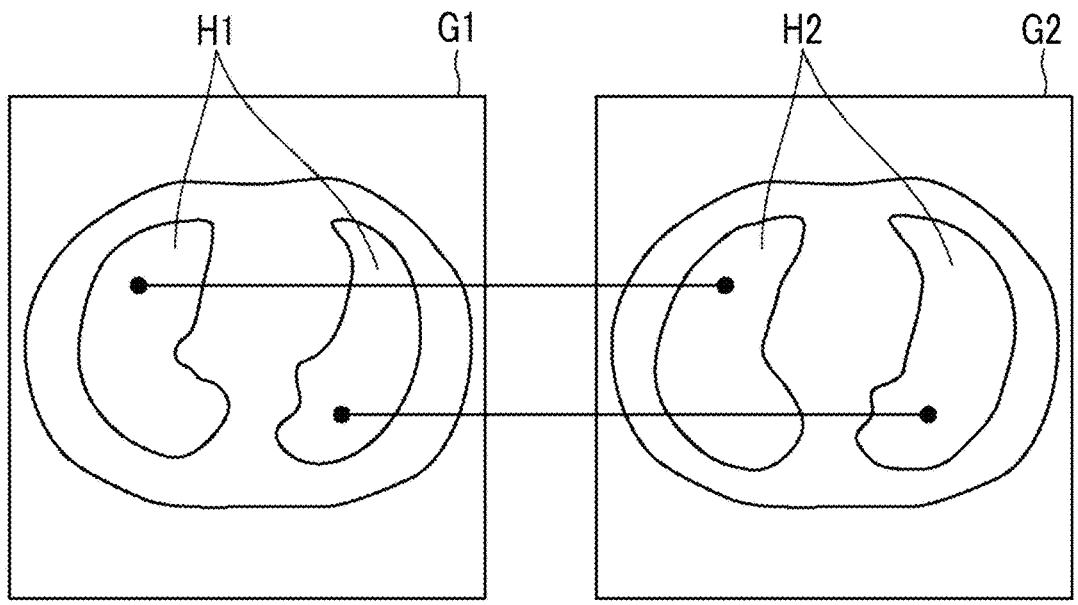
FIG. 3 is a view illustrating registration of lung field regions.

By performing registration in this manner, as shown in FIG. 3, each pixel of a lung field region H1 of the first medical image G1 and each pixel of a lung field region H2 of the second medical image G2 (indicated by a black circle in FIG. 3) are associated with each other. Further, with the registration, the number of pixels included in the lung field region H1 and the number of pixels included in the lung field region H2 can be regarded as the same. Since registration of all the regions of the first medical image G1 and the second medical image G2 is performed so that registration is performed between the lung field region H1 and the lung field region H2, registration of all the regions of the first medical image G1 and the second medical image G2 may be performed.

The property classification unit 23 classifies each pixel of the lung field regions H1 and H2 of the first and second medical images G1 and G2 into any one of a plurality of types of properties. Specifically, the property classification unit 23 derives a plurality of evaluation values indicating the possibility of being each of a plurality of types of tissues or lesions (that is, properties) for each pixel of the lung field regions H1 and H2, and classifies each pixel of the lung field regions H1 and H2 into any one of the plurality of types of properties based on the plurality of evaluation values.

The property classification unit 23 of the present embodiment has a discriminative model 30 consisting of a multi-layer neural network generated by deep learning, which is one of machine learning methods, and classifies each pixel of the lung field regions H1 and H2 into any one of the plurality of properties using the discriminative model 30. A machine learning method is not limited to deep learning, and other methods, such as a support vector machine, can be used.

In the multi-layer neural network, in each layer, arithmetic processing is performed using various kernels on data of a plurality of different feature amounts obtained by the previous layer (regarding a first layer, pixel data in the lung field regions H1 and H2). Then, in the subsequent layers, arithmetic processing is further performed on the data of the feature amounts obtained by the arithmetic processing, so that the recognition rate of the feature amounts can be improved and the input data can be classified into a plurality of classes.

In the present embodiment, description will be made using the multi-layer neural network that receives, as an input, the lung field regions H1 and H2 as three-dimensional images and that outputs the result of classification into any one of the plurality of types of properties for each pixel of the lung field regions H1 and H2. However, a configuration can be adopted in which the lung field region as a two-dimensional image in each of the plurality of tomographic images constituting the first and second medical images G1 and G2 is received as an input and the result of classification into the plurality of types of properties for the lung field region as the two-dimensional image is output.

Figure 4:
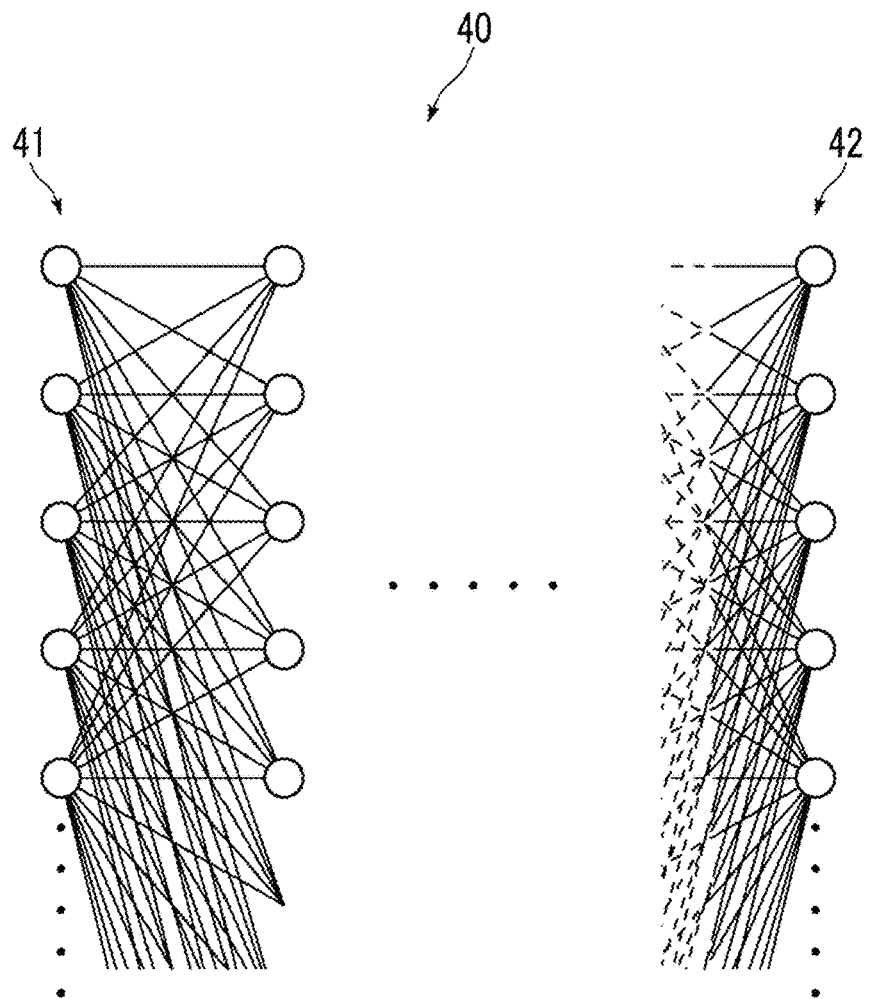
FIG. 4 is a view showing an example of a multi-layer neural network.

FIG. 4 is a view showing an example of the multi-layer neural network. As shown in FIG. 4, a multi-layer neural network 40 consists of a plurality of layers including an input layer 41 and an output layer 42. In the present embodiment, the multi-layer neural network 40 learns to classify each pixel of the lung field regions H1 and H2 into any one of 33 types of properties, such as normal lung, GGO mass nodule opacity, mixed mass nodule opacity, solid mass nodule opacity, ground glass opacity, pale ground glass opacity, centrilobular ground glass opacity, consolidation, low density, centrilobular emphysema, panlobular emphysema, normal pulmonary emphysema tendency, cyst, tree-in-bud (TIB), small nodule (non-centrilobular), centrilobular small nodule opacity, interlobular septal thickening, bronchial wall thickening, bronchiectasis, bronchioloectasis, air bronchogram, traction bronchiectasis, cavity consolidation, cavernous tumor, reticular opacity, fine reticular opacity, honeycomb lung, pleural effusion, pleural thickening, chest wall, heart, diaphragm, and blood vessel. The property types are not limited thereto, and more or fewer properties than the above properties may be used.

In the present embodiment, the multi-layer neural network 40 learns the properties using a large amount of training data, such as millions of pieces of training data. Upon learning, a region of interest with a predetermined size (for example, 1.5 cm×1.5 cm×1.5 cm) is cut out from a CT image in which the property type is known, and the region of interest is used as the training data. Then, the training data is input to the multi-layer neural network 40, and the multi-layer neural network 40 outputs the classification result of the property type. Then, the output classification result is compared with the training data, and the weight of connection between the layers of units (indicated by circles in FIG. 4) included in each layer of the multi-layer neural network 40 is corrected from the output side to the input side in response to whether or not the output result is correct or incorrect. The correction of the weight of the connection is repeated using a large amount of training data a predetermined number of times or until the accuracy rate of the output classification result reaches 100%, and the learning ends. As a result, the discriminative model 30 is constructed.

Further, in a case in which the input image is a tomographic image, upon the learning by the multi-layer neural network 40, a two-dimensional region normalized to a predetermined size (for example, 1.5 cm×1.5 cm) is cut out from a tomographic image constituting a three-dimensional image in which the lesion is known, and the image of the cut-out two-dimensional region is used as the training data.

The property classification unit 23 extracts the lung field regions H1 and H2, which are target regions, from the first and second medical images G1 and G2 in order to classify the properties. As a method of extracting the lung field regions H1 and H2, any method such as a method in which the signal value of each pixel in the first and second medical images G1 and G2 is expressed in a histogram and threshold processing is performed to extract the lung or a region growing method based on a seed point showing the lung can be used. The discriminative model 30 in which machine learning has been performed so as to extract the lung field regions H1 and H2 may be used.

In the property classification unit 23, upon the property classification processing, a region of interest having the same size as the training data is sequentially cut out from the lung field regions H1 and H2, and the region of interest is input to the discriminative model 30 consisting of the multi-layer neural network 40. With this, the discriminative model 30 outputs an evaluation value corresponding to each classification of the properties for the central pixel of the cut-out region of interest. The evaluation value corresponding to each classification is an evaluation value indicating the probability of the central pixel belonging to each classification. The larger this evaluation value is, the higher the probability that the central pixel belongs to the classification is.

FIG. 5 is a view showing evaluation values corresponding to property types for a certain pixel. In addition, in FIG. 5, the evaluation values for a part of the properties are shown for simplicity of illustration. In the present embodiment, the discriminative model 30 classifies the central pixel of the region of interest into a property with the maximum evaluation value out of the plurality of properties. For example, in a case in which the evaluation values shown in FIG. 5 are acquired, the central pixel of the region of interest has the highest probability of being reticular opacity and has the second highest probability of being ground glass opacity. On the contrary, the probability of the central pixel being normal lung or low density is almost zero. Therefore, in a case in which the evaluation values as shown in FIG. 5 are acquired, the central pixel of the region of interest is classified into reticular opacity having a maximum evaluation value of 8.5 by the property classification processing. Such property classification processing is performed on all the pixels of the lung field regions H1 and H2, so that all the pixels of the lung field regions H1 and H2 are classified into any one of the plurality of types of properties.

In the present embodiment, although the property classification unit 23 classifies each pixel of the lung field regions H1 and H2 into any one of 33 types of properties as described above, in order to simplify arithmetic operation for generating a mapping image and deriving the quantitative value, which will be described later, in the present embodiment, 33 types of properties are summarized into 10 types of properties, that is, normal opacity, ground glass opacity, reticular opacity, consolidation, honeycomb lung, nodular opacity, hyperlucent lung, others, bronchus, and blood vessel. The types of properties to be summarized are not limited to these 10 types, and may be more than 10 or less than 10.

Figure 6:
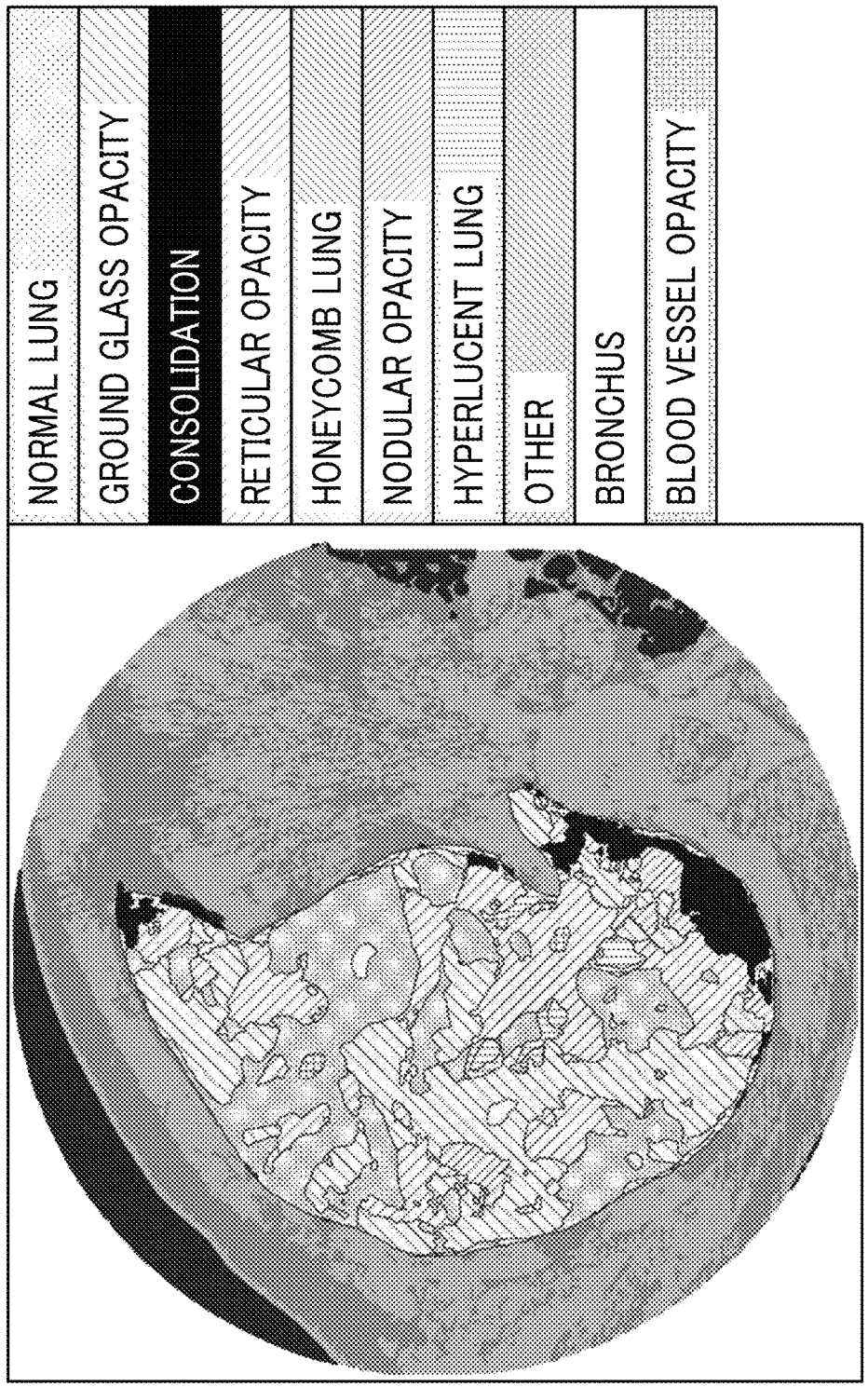
FIG. 6 is a view showing a cross-section in a mapping image in which colors corresponding to classifications are assigned.

The property classification unit 23 generates a mapping image by assigning a color to the pixel of each classification in at least one of the first medical image G1 or the second medical image G2, based on the result of the property classification processing. Specifically, the property classification unit 23 generates a three-dimensional mapping image by assigning the same color to the pixels classified into the same property, for all the pixels in a three-dimensional space classified into any one of the plurality of types of properties that are summarized into 10 types as described above. FIG. 6 is a view showing a cross-section in a mapping image in which colors corresponding to a plurality of types of classifications are assigned for each classification. The display control unit 25, which will be described later, may display the mapping image on the display unit 14. In a case in which the mapping image is displayed on the display unit 14, as shown in FIG. 6, a cross-sectional image of any cross-section in the three-dimensional mapping image may be displayed. However, the present disclosure is not limited thereto, and the three-dimensional mapping image may be displayed on the display unit 14 by a method such as volume rendering.

The quantitative value derivation unit 24 specifies property pairs each representing a property change between the corresponding pixels in at least partial regions of the lung field regions H1 and H2 of the first and second medical images G1 and G2, and derives the quantitative value in the at least partial regions for each of the property pairs. In the present embodiment, the quantitative value derivation unit 24 specifies property pairs in all the regions of the lung field regions H1 and H2, and derives the ratio in the lung field regions H1 and H2 for each of the property pairs as the quantitative value.

In the present embodiment, the property classification unit 23 classifies each pixel of the lung field regions H1 and H2 into any one of 10 types of properties. Here, in a case in which the property of a certain pixel in the lung field region H1 is normal opacity, the property that the pixel may take in the lung field region H2 of the second medical image G2 of which the imaging time is later than the imaging time of the first medical image G1 is 10 types, that is, normal opacity, ground glass opacity, reticular opacity, consolidation, honeycomb lung, nodular opacity, hyperlucent lung, other, bronchus, and blood vessel. Therefore, 10×10=100 combinations of property changes exist between the corresponding pixels of the lung field regions H1 and H2, as the property pair. Accordingly, the quantitative value derivation unit 24 specifies which of the 100 property pairs each pixel of the lung field regions H1 and H2 corresponds to.

Further, the quantitative value derivation unit 24 counts the number of pixels in the lung field regions H1 and H2 for all the property pairs. Then, the quantitative value derivation unit 24 divides the number of pixels for each property pair by the total number of pixels in the lung field regions H1 and H2 to derive the ratio of each property pair to all the regions in the lung field regions H1 and H2 as the quantitative value. FIG. 7 is a view showing the derivation result of the quantitative value. The rows in FIG. 7 represent the properties of the lung field region H2 of the second medical image G2, and the columns represent the properties of the lung field region H1 of the first medical image G1. In addition, in FIG. 7, the property pairs of the fields positioned diagonally are each a property pair in which there is no change in the property between the lung field region H1 and the lung field region H2.

The display control unit 25 displays the quantitative value for each of the property pairs on the display unit 14. FIG. 8 is a view showing a display screen of the quantitative value for each of the property pairs. As shown in FIG. 8, a display screen 50 displays a list 51 of the quantitative value for each of the property pairs. Here, in a case in which a property pair representing that the symptom is worsened, out of the property pairs, has a value as the quantitative value (that is, in a case in which the quantitative value is not 0%, the same applies hereinafter), the field of the property pair is displayed in a different form from the other fields. For example, a field having a value as the quantitative value is colored, or the color of a number in the field is changed. In the list 51 shown in FIG. 8, the field of the property pair in which the symptom is worsened is colored. In FIG. 8, the field to be colored is shown by hatching. Further, the mapping image shown in FIG. 6, in addition to the list 51, may be displayed on the display screen 50.

Although which property change corresponds to the worsening of the symptom differs depending on the disease, in interstitial pneumonia, the symptom is generally worsened in the order of normal opacity, ground glass opacity, reticular opacity, and honeycomb lung. In addition, the bronchus and the blood vessel are tissues that also exist in the normal lung field, but normal opacity may be changed to the bronchus and the blood vessel because the bronchus dilates or the blood vessel dilates in a case in which the symptom is worsened.

In the present embodiment, as shown in FIG. 8, the property pairs of (normal opacity, ground glass opacity), (ground glass opacity, reticular opacity), (reticular opacity, honeycomb lung), (normal opacity, hyperlucent lung), and (normal opacity, bronchus) have values as the quantitative value. Therefore, for example, a red color is given to the fields of the property pairs so that the worsened symptom can be visually recognized.

On the other hand, in a case in which the property other than normal opacity in the lung field region H1 of the first medical image G1 is changed to normal opacity in the second medical image G2, the property pair represents that the symptom is improved. Therefore, in a case in which the property pairs of (ground glass opacity, normal lung), (reticular opacity, normal lung), (consolidation, normal lung), (honeycomb lung, normal lung), (hyperlucent lung, normal lung), (nodular opacity, normal lung), (other, normal lung), (bronchus, normal lung), and (blood vessel, normal lung), which are the property pairs representing that the symptom is improved, have values as the ratio, for example, a blue color is given to the field so that the improved symptom may be visually recognized. In addition to the above property pairs, examples of the property pair in which the symptom is improved include (reticular opacity, ground glass opacity). In addition, the property pair in which there is no change in the symptom may not be colored or may be given a gray color.

The interpretation of the worsening and improvement of the symptom may differ depending on the doctor. Therefore, it is preferable to allow the doctor to set which property pair is the property pair representing property changes of the worsening and improvement.

Figure 9:
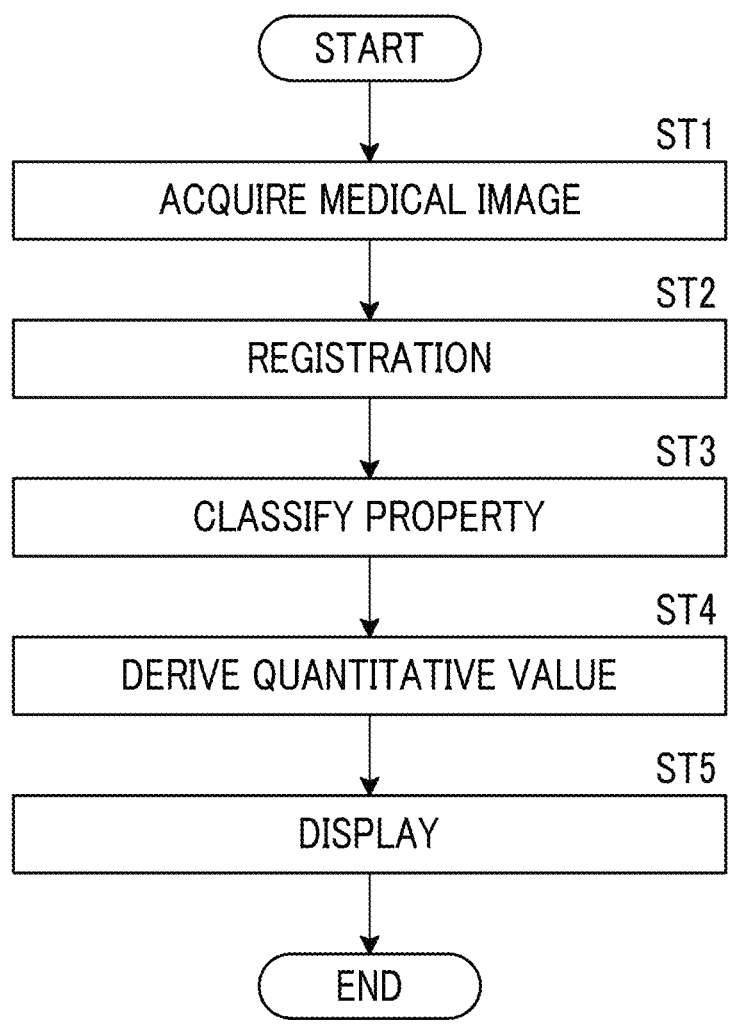
FIG. 9 is a flowchart showing processing performed in the present embodiment.

Next, processing performed in the present embodiment will be described. FIG. 9 is a flowchart showing processing performed in the present embodiment. First, the image acquisition unit 21 acquires the first and second medical images G1 and G2 (medical image acquisition; step ST1), and the registration unit 22 performs registration of the lung field region H1 of the first medical image G1 and the lung field region H2 of the second medical image G2 (step ST2). Further, the property classification unit 23 classifies each pixel included in the lung field region H1 of the first medical image G1 and the lung field region H2 of the second medical image G2 into any one of the plurality of types of properties (step ST3). The processing of step ST2 and step ST3 may be performed in parallel, or the processing of step ST3 may be performed before the processing of step ST2.

Next, the quantitative value derivation unit 24 specifies property pairs each representing a property change between the corresponding pixels in the lung field regions H1 and H2, and derives the ratio in at least partial regions for each of the property pairs as the quantitative value (quantitative value derivation; step ST4). Then, the display control unit 25 displays the quantitative value for each of the property pairs on the display unit 14 (step ST5), and the processing ends.

As described above, in the present embodiment, in the lung field regions H1 and H2 of the first and second medical images G1 and G2, the property pairs each representing a property change between the corresponding pixels are specified, and the ratio in the lung field regions H1 and H2 for each of the property pairs is derived as the quantitative value. Therefore, according to the present embodiment, the derived quantitative values are displayed, so that it is possible to recognize the tendency of property changes in the lung field regions H1 and H2. Consequently, according to the present embodiment, it is possible to accurately recognize the property changes between the first and second medical images G1 and G2 having different imaging times.

In the above embodiment, colors corresponding to the magnitude of the quantitative values may be assigned, for each field of the property pairs of the list 51 of the quantitative values. For example, a ratio of 0% may be assigned a gray color, a ratio of 0% to 5% (greater than 0% and 5% or less, the same applies hereinafter) may be assigned a yellow color, a ratio of 5% to 20% may be assigned an orange color, and a ratio of greater than 20% may be assigned a red color. FIG. 10 is a view showing a display screen of a list in which colors corresponding to the magnitude of the quantitative values are assigned, for each field of the property pairs. In addition, in FIG. 10, the difference between the colors is shown by a difference in hatching. Further, in this case as well, the color may be further changed in accordance with the property pair representing that the lesion is worsened, the property pair representing that the lesion is improved, and the property pair in which there is no change in the lesion. For example, a reddish color may be assigned to the property pair representing that the lesion is worsened, and a bluish color may be assigned to the property pair representing that the lesion is improved.

Figure 11:
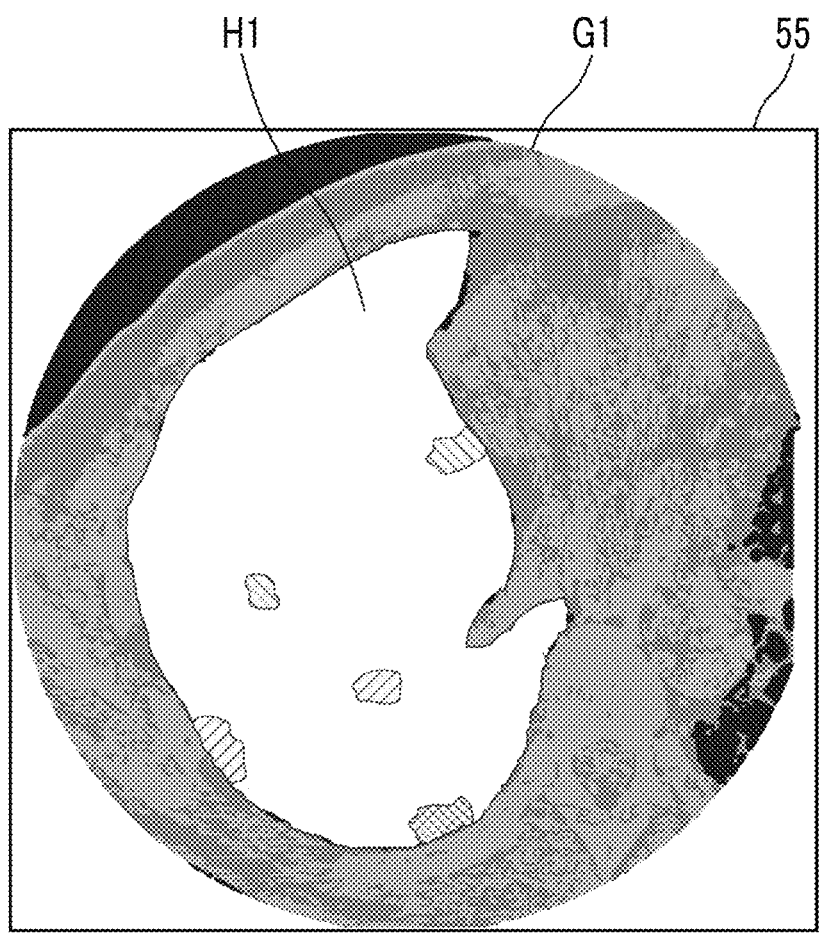
FIG. 11 is a view showing a display screen in which information representing the quantitative value is superimposed and displayed on a medical image.

Further, in the above embodiment, information representing the quantitative value for at least a part of the property pairs may be superimposed and displayed on the first medical image G1 or the second medical image G2. FIG. 11 is a view showing a display screen in which information representing the quantitative value is superimposed and displayed on a medical image. As shown in FIG. 11, a newly captured first medical image G1 is displayed on a display screen 55, and colors corresponding to the magnitude of the quantitative values are assigned to the regions including pixels having values as the quantitative value, out of the property pairs, for each pixel of the lung field region H1 of the first medical image G1. For example, a ratio of 0% may not be colored, a ratio of 0% to 5% may be assigned a yellow color, a ratio of 5% to 20% may be assigned an orange color, and a ratio of greater than 20% may be assigned a red color. In FIG. 11, a difference between the colors is represented by a difference in hatching.

Further, in the above embodiment, the quantitative value derivation unit 24 may derive the amount of change per short time in the ratio of the property pair as the quantitative value by dividing the derived ratio by a difference in acquisition time between the first medical image G1 and the second medical image G2. For example, in a case in which the difference in acquisition time between the first medical image G1 and the second medical image G2 is 3 months, the quantitative value derivation unit 24 can derive the amount of change in the ratio of the property pair per month by dividing the derived ratio by 3.

Further, in the above embodiment, all the property pairs are included and displayed in the list 51, but the present disclosure is not limited thereto. Only the property pair representing the property change in which the symptom is worsened may be displayed in the list, only the property pair representing the property change in which the symptom is improved may be displayed in the list, or only the property pair representing that there is no change in the symptom may be displayed in the list. Alternatively, the property pair representing the property change in which the symptom is worsened, the property pair representing the property change in which the symptom is improved, and the property pair representing that there is no change in the symptom may be displayed in a switchable manner.

Figures 12, 13:
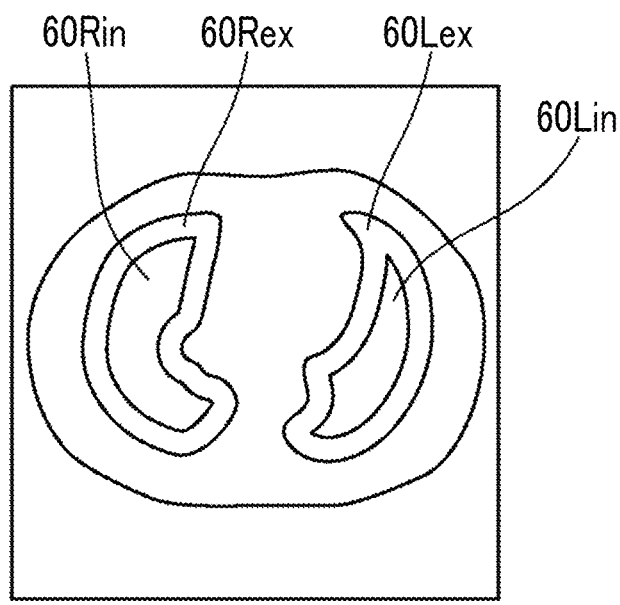
FIG. 12 is a view showing a display screen in which the property pairs are ranked and displayed in descending order of the quantitative values.
FIG. 13 is a view illustrating the division of the lung field region into an inner region and an outer region.

Further, in the above embodiment, the quantitative values may be displayed in descending order of the quantitative values of the property pairs. FIG. 12 is a view showing a display screen in which the property pairs are ranked and displayed in descending order of the quantitative values. As shown in FIG. 12, the property pairs are ranked and displayed from the first place to the fifth place in descending order of the quantitative values on a display screen 58. With this, it is possible to easily recognize which property pair is more in the first and second medical images G1 and G2.

Figure 14:
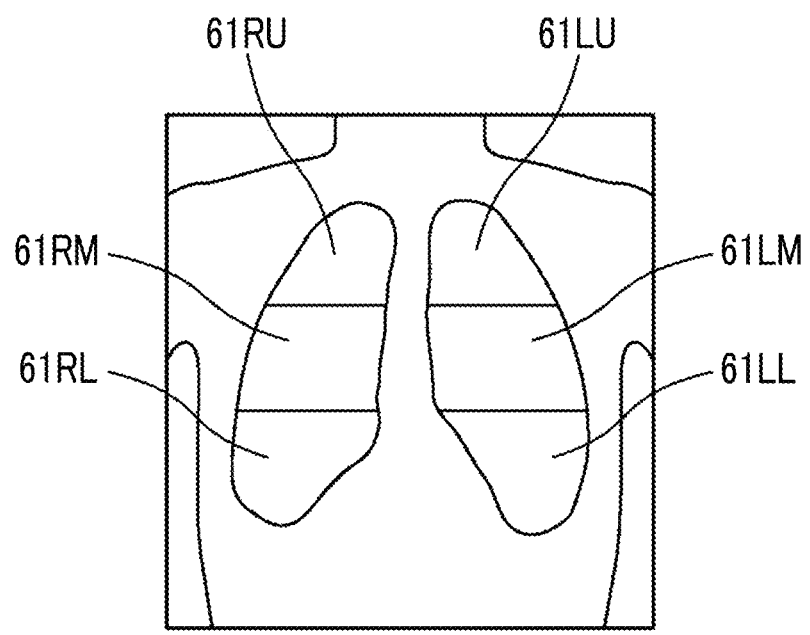
FIG. 14 is a view illustrating the division of the lung field region into an upper region, a middle region, and a lower region.

Further, in the above embodiment, property pairs are derived for all the regions of the lung field regions H1 and H2 of the first and second medical images G1 and G2, and the quantitative values are displayed, but the present disclosure is not limited thereto. The lung field regions H1 and H2 can be divided into a left lung and a right lung. Further, each of the left and right lungs can be divided into an upper lobe, a middle lobe, and a lower lobe. Alternatively, as shown in FIG. 13, the lung field region can be divided into inner regions 60Lin and 60Rin, and outer regions 60Lex and 60Rex for the left lung and the right lung, respectively. Alternatively, as shown in FIG. 14, the lung field region can be divided into three regions of upper, middle, and lower regions. That is, the left lung can be divided into an upper region 61LU, a middle region 61LM, and a lower region 61LL, and the right lung can be divided into an upper region 61RU, a middle region 61RM, and a lower region 61RL. Alternatively, the lung field region can be divided into a dorsal region and a ventral region. Alternatively, the lung field region can be divided into a central region near the first branch of the bronchus and a region other than the central region. Therefore, the lung field regions H1 and H2 may be divided into small regions as described above, and the quantitative values of the property pairs may be derived and displayed for each small region. The mode of division is not limited to the above modes. The lung field region may be divided in combination with a plurality of division modes. For example, in addition to the division of the inner region and the outer region, the division of three regions of upper, middle, and lower regions may be performed, and in addition thereto or instead thereof, the division into the dorsal region and the ventral region may be performed.

Further, in the above embodiment, the quantitative value derivation unit 24 derives the ratio in at least partial regions for each of the property pairs as the quantitative value, but the present disclosure is not limited thereto. The volume (in a case of a three-dimensional image), the area (in a case of a tomographic image), or the number of pixels in at least partial regions for each of the property pairs may be derived as the quantitative value.

Further, in the above-described embodiment, for example, the following various processors can be used as a hardware structure of a processing unit that executes various processing, such as the image acquisition unit 21, the registration unit 22, the property classification unit 23, the quantitative value derivation unit 24, and the display control unit 25. The various processors include, for example, a programmable logic device (PLD), such as a field programmable gate array (FPGA), which is a processor having a changeable circuit configuration after manufacture, and a dedicated electrical circuit, such as an application specific integrated circuit (ASIC), which is a processor having a dedicated circuit configuration designed to perform specific processing, in addition to the CPU, which is a general-purpose processor that executes software (programs) to function as various processing units as described above.

One processing unit may be constituted of one of the various processors or may be constituted of a combination of two or more processors of the same type or different types (for example, a combination of a plurality of FPGAs and a combination of a CPU and an FPGA). Alternatively, the plurality of processing units may be constituted of one processor.

A first example of the configuration in which the plurality of processing units are constituted of one processor is an aspect in which one or more CPUs and software are combined to constitute one processor and the processor functions as a plurality of processing units. A representative example of the aspect is a computer such as a client and server. A second example of the configuration is an aspect in which a processor that implements all of the functions of a system including the plurality of processing units with one integrated circuit (IC) chip is used. A representative example of the aspect is a system on chip (SoC). As described above, as the hardware structure of various processing units, one or more of the various processors are used.

Furthermore, as the hardware structure of the various processors, more specifically, an electrical circuit (circuitry) in which circuit elements, such as semiconductor elements, are combined can be used.

EXPLANATION OF REFERENCES

1: image processing device
2: three-dimensional image capturing device
3: image storage server
4: network
11: CPU
12: memory
13: storage
14: display unit
15: input unit
21: image acquisition unit
22: registration unit
23: property classification unit
24: quantitative value derivation unit
25: display control unit
30: discriminative model
40: multi-layer neural network
41: input layer
42: output layer
50, 55, 58: display screen
60Rin, 60Lin: inner region
60Rex, 60Lex: outer region
61RU, 61LU: upper region
61RM, 61LM: middle region
61RL, 61LL: lower region
G1: first medical image
G2: second medical image
H1, H2: lung field region

What is claimed is:

1. An image processing device comprising a processor, the processor configured to:
   classify each pixel included in a target region of each of a first medical image and a second medical image of which an imaging time is later than an imaging time of the first medical image for the same subject into any one of a plurality of types of properties; and
   specify property pairs each representing a property change between corresponding pixels in at least partial regions within the target regions, and derive a quantitative value in the at least partial regions for each of the property pairs,
   wherein each of the property pairs comprises a combination of a first type of property for the first medical image and a second type of property for the second medical image that are derived in the target regions included in the first medical image and the second medical image and different from each other.

2. The image processing device according to claim 1, wherein the processor is configured to derive a ratio in the at least partial regions for each of the property pairs as the quantitative value.

3. The image processing device according to claim 1, the processor further configured to
   perform registration of the target regions between the first medical image and the second medical image.

4. The image processing device according to claim 1, wherein the processor is configured to derive an amount of change per unit time in an amount of the property pair between the corresponding pixels in the at least partial regions as the quantitative value.

5. The image processing device according to claim 1, wherein the processor is configured to divide the target region into a plurality of small regions and derive the quantitative value for each of the small regions.

6. The image processing device according to claim 1, the processor further configured to
   display the quantitative value for each of the property pairs on a display.

7. The image processing device according to claim 6, wherein the processor is configured to display the quantitative value such that a property pair in which a symptom is worsened, a property pair in which the symptom is improved, and a property pair in which there is no change in the symptom, out of the property pairs, can be identified.

8. The image processing device according to claim 6, wherein the processor is configured to display the quantitative value for each of the property pairs in descending order of the quantitative values.

9. The image processing device according to claim 6, wherein the processor is configured to superimpose and display information representing the quantitative value for at least a part of the property pairs, on the target region of the first medical image or the second medical image.

10. The image processing device according to claim 1, wherein the processor is configured to have a discriminative model in which machine learning has been performed so as to classify the plurality of types of properties, and classify each pixel included in the target region into any one of the plurality of types of properties via the discriminative model.

11. The image processing device according to claim 1, wherein the target region is a lung field region.

12. The image processing device according to claim 1, wherein the property pairs include a pair of same properties and a pair of different properties.

13. An image processing method comprising:
classifying each pixel included in a target region of each of a first medical image and a second medical image of which an imaging time is later than an imaging time of the first medical image for the same subject into any one of a plurality of types of properties; and
specifying property pairs each representing a property change between corresponding pixels in at least partial regions within the target regions, and deriving a quantitative value in the at least partial regions for each of the property pairs,
wherein each of the property pairs comprises a combination of a first type of property for the first medical image and a second type of property for the second medical image that are derived in the target regions included in the first medical image and the second medical image and different from each other.

14. A non-transitory computer recording medium storing an image processing program causing a computer to execute a process comprising:
classifying each pixel included in a target region of each of a first medical image and a second medical image of which an imaging time is later than an imaging time of the first medical image for the same subject into any one of a plurality of types of properties; and
specifying property pairs each representing a property change between corresponding pixels in at least partial regions within the target regions, and deriving a quantitative value in the at least partial regions for each of the property pairs,
wherein each of the property pairs comprises a combination of a first type of property for the first medical image and a second type of property for the second medical image that are derived in the target regions included in the first medical image and the second medical image and different from each other.

* * * * *